(12) United States Patent
Xia et al.

(10) Patent No.: US 7,094,918 B2
(45) Date of Patent: Aug. 22, 2006

(54) LOW-COLOR ULTRAVIOLET ABSORBERS FOR THERMOPLASTIC AND THERMOSET HIGH UV WAVELENGTH PROTECTION APPLICATIONS

(75) Inventors: Jusong Xia, Spartanburg, SC (US); Mary E. Mason, Spartanburg, SC (US); Eric B. Stephens, Roebuck, SC (US)

(73) Assignee: Milliken & Company, Spartanburg, SC (US)

( * ) Notice: Subject to any disclaimer, the term of this patent is extended or adjusted under 35 U.S.C. 154(b) by 336 days.

(21) Appl. No.: 10/424,472

(22) Filed: Apr. 28, 2003

(65) Prior Publication Data

US 2004/0214934 A1  Oct. 28, 2004

(51) Int. Cl.
| | |
|---|---|
| C07C 69/74 | (2006.01) |
| C03C 17/00 | (2006.01) |
| C08K 5/10 | (2006.01) |
| C08L 1/00 | (2006.01) |
| C09K 3/00 | (2006.01) |

(52) U.S. Cl. ............... 558/401; 588/392; 588/288; 524/315; 524/205; 524/366; 524/367; 524/368; 524/369; 523/160; 560/1; 568/593; 568/608; 568/657

(58) Field of Classification Search ............ 558/401, 558/392
See application file for complete search history.

(56) References Cited

U.S. PATENT DOCUMENTS

| | | | |
|---|---|---|---|
| 3,201,363 A | 8/1965 | Spurlin et al. | 260/30.4 |
| 3,207,736 A | 9/1965 | Wijga et al. | 260/93.7 |
| 3,234,233 A | 2/1966 | Bolger et al. | 260/326 |
| 3,320,267 A | 5/1967 | Poos et al. | 260/295 |
| 3,367,926 A | 2/1968 | Voeks et al. | 260/93.5 |
| 3,527,736 A | 9/1970 | Averink et al. | 260/78.4 |
| 3,546,270 A | 12/1970 | Kirchmayr et al. | 260/465 |
| 3,634,320 A | 1/1972 | Wetzner et al. | 260/45.85 R |
| 3,793,401 A | 2/1974 | Nield et al. | 260/876 |
| 3,809,707 A | 5/1974 | Havinga et al. | 260/404 |
| 3,829,450 A | 8/1974 | Schmerling et al. | 260/346.3 |
| 3,873,643 A | 3/1975 | Wu et al. | 260/878 |
| 3,880,992 A | 4/1975 | Smolin et al. | 424/60 |
| 3,882,194 A | 5/1975 | Krebaum et al. | 260/878 |
| 3,928,687 A | 12/1975 | Wada et al. | 428/461 |
| 3,933,779 A | 1/1976 | Baron et al. | 260/93.5 |
| 3,941,746 A | 3/1976 | Stephen et al. | 260/45.8 |
| 3,954,913 A | 5/1976 | Uebele et al. | 260/880 |
| 4,039,491 A | 8/1977 | Ikeda et al. | 260/875 |
| 4,134,895 A | 1/1979 | Roth et al. | 260/326 |
| 4,134,927 A | 1/1979 | Tomoshige et al. | 260/878 |
| 4,284,729 A | 8/1981 | Cross et al. | 521/158 |
| 4,452,942 A | 6/1984 | Shida et al. | 525/74 |
| 4,476,184 A | 10/1984 | Lubowitz et al. | 428/288 |
| 4,496,757 A | 1/1985 | Dexter et al. | 560/82 |
| 4,503,219 A | 3/1985 | Reffert et al. | 528/481 |
| 4,617,374 A | 10/1986 | Pruett et al. | 528/288 |
| 4,619,990 A | 10/1986 | Elmasry | 534/573 |
| 4,704,421 A | 11/1987 | Teskin | 524/287 |
| 4,732,570 A | 3/1988 | Baumgartner et al. | 8/506 |
| 4,739,017 A | 4/1988 | Tabor et al. | 525/300 |
| 4,778,837 A | 10/1988 | Waterman et al. | 524/89 |
| 4,801,637 A | 1/1989 | McCullough et al. | 524/287 |
| 4,829,114 A | 5/1989 | Trotoir et al. | 524/243 |
| 4,845,188 A | 7/1989 | Weaver et al. | 528/272 |
| 4,920,169 A | 4/1990 | Avar | 524/219 |
| 5,013,778 A | 5/1991 | Bath et al. | 524/173 |
| 5,057,627 A | 10/1991 | Edwards | 568/618 |
| 5,075,491 A | 12/1991 | Weaver et al. | 560/45 |
| 5,135,975 A | 8/1992 | Rekers et al. | 524/108 |
| 5,342,868 A | 8/1994 | Kimura et al. | 524/108 |
| 5,442,086 A | 8/1995 | Krutak et al. | 558/401 |
| 5,491,187 A | 2/1996 | Ward et al. | 524/159 |
| 5,543,083 A | 8/1996 | Sivik et al. | 252/403 |
| 5,922,793 A | 7/1999 | Amos et al. | 524/159 |
| 5,929,146 A | 7/1999 | Amos et al. | 524/89 |
| 5,981,636 A | 11/1999 | Amos et al. | 524/108 |

(Continued)

FOREIGN PATENT DOCUMENTS

DE    1 544 851    5/1970

(Continued)

OTHER PUBLICATIONS

H.N. Beck, "Heterogeneous Nucleating Agents of Polypropylene Crystallization", Journal of Applied Polymer Science, vol. 11, pp. 673-685, 1967.

(Continued)

*Primary Examiner*—Joseph D. Anthony
(74) *Attorney, Agent, or Firm*—Terry T. Moyer; John E. Vick, Jr.

(57) ABSTRACT

Novel ultraviolet absorbing compounds that are liquid in nature, are low in color (and thus permit use without the concomitant necessity of adding large amounts of other coloring agents to combat such discoloring), and are highly effective in providing protection in wavelength ranges for which previous attempts at low-color ultraviolet absorbers have failed are provided herein. Such compounds provide such excellent, inexpensive, and beneficial protection from ultraviolet exposure within various media, including, but not limited to, clear thermoplastics. The particular compounds are generally polymeric in nature including various chain lengths of polyoxyalkylenes thereon and are liquid in nature to facilitate handling and introduction within the target media. In addition, such ultraviolet absorbers also exhibit extremely low migratory properties thereby providing long-term protective benefits to the target media as well. This invention also concerns the end products, specific broadly defined types of compounds providing such beneficial characteristics, methods of making such low-color compounds, and methods of producing such clear, UV protected end products.

1 Claim, No Drawings

U.S. PATENT DOCUMENTS

| | | | |
|---|---|---|---|
| 6,096,811 A | 8/2000 | Amos et al. ................ 524/89 |
| 6,207,740 B1 * | 3/2001 | Zhao et al. ................ 524/366 |
| 6,559,216 B1 * | 5/2003 | Zhao et al. ................ 524/366 |
| 6,596,795 B1 * | 7/2003 | Zhao et al. ................ 524/205 |
| 6,602,447 B1 * | 8/2003 | Danielson et al. ......... 252/589 |
| 6,891,058 B1 * | 5/2005 | Zhao et al. ................ 558/401 |
| 2002/0065042 A1 | 5/2002 | Picoult et al. |
| 2002/0065101 A1 | 5/2002 | Picoult et al. |
| 2002/0080386 A1 | 6/2002 | Snowdon et al. |
| 2003/0136949 A1 * | 7/2003 | Danielson et al. ......... 252/588 |

FOREIGN PATENT DOCUMENTS

| | | | |
|---|---|---|---|
| DE | 1 694 914 B | 3/1972 | |
| EP | 0267 695 | 5/1988 | |
| EP | 0336 573 | 3/1989 | |
| FR | 2 075 549 | 9/1971 | |
| FR | 2 656 620 | 7/1991 | |
| GB | 2 290 296 | 12/1995 | |
| JP | 53-40760 | 4/1978 | ........ 548/435 |
| JP | 57-18682 | 1/1982 | |
| JP | 58-160343 | 9/1983 | |
| JP | 60-13837 | 1/1985 | |
| JP | 61-17834 | 5/1986 | |
| JP | 01-180514 | 7/1989 | |
| JP | 03-076815 A | 4/1991 | |
| JP | 05-139460 | 6/1993 | |
| JP | 07-173342 | 7/1995 | |

OTHER PUBLICATIONS

Overman et al., "An Annual Publication of Satisfactory Methods for the Preparation of Organic Chemicals." Organic Synthesis, vol. 71, pp. 48-55, 1993.

Snider et al., "Mn(III)-Based Oxidative Free Radical Cyclization of Unsaturated Ketones," Journal of Organic Chemistry, vol. 60, pp. 5376-5377, 1995.

Fillon et al., "Self-Nucleation and Recrystallization of Isotactic Polypropylene (alpa Phase) Investigated by Differential Scanning Calorimetry," Journal of Polymer Science: Part B: Polymer Physics, vol. 31, pp. 1383-1393, 1993.

Fillon et al., "Self-Nucleation and Enhanced Nucleation of Polymers. Definition of a Convenient Calorimetric "Efficiency Scale" and Evaluation of Nucleating Additives in Isotactic Polypropylene (alpha phase)," Journal of Polymer Science: Part B: Polymer Physics, vol. 31 pp. 1395-1504, 1993.

* cited by examiner

LOW-COLOR ULTRAVIOLET ABSORBERS FOR THERMOPLASTIC AND THERMOSET HIGH UV WAVELENGTH PROTECTION APPLICATIONS

FIELD OF THE INVENTION

This invention relates to novel ultraviolet absorbing compounds that are liquid in nature, are low in color (and thus permit use without the concomitant necessity of adding large amounts of other coloring agents to combat any discoloring within clear, colorless applications), and are highly effective in providing protection in wavelength ranges for which previous attempts at low-color ultraviolet absorbers have failed. Such compounds provide excellent, inexpensive, and beneficial protection from ultraviolet exposure within various media, including, but not limited to, clear thermoplastics. The particular compounds are generally polymeric in nature including various chain lengths of polyoxyalkylenes thereon and are liquid in nature to facilitate handling and introduction within the target media. In addition, such ultraviolet absorbers also exhibit extremely low migratory properties thereby providing long-term protective benefits to the target media as well. This invention also concerns the end products, specific broadly defined types of compounds providing such beneficial characteristics.

BACKGROUND OF THE PRIOR ART

All of the U.S. patents cited throughout this specification are hereby entirely incorporated herein.

Ultraviolet absorber compounds have been utilized for a number of protective applications, including within compositions for covering skin, on and within apparel and other types of textiles, within transparent plastic containers, and the like, to combat the harmful and degradable effects of certain wavelengths of light in the UV spectrum. The best known UV absorbers are benzotriazoles, available from Ciba under the tradename Tinuvin®, and benzophenones, available from Cytec Industries under the trademark Cyasorb™. Such compounds are highly effective in their UV absorber capacity; however, they are quite costly, can prove difficult to incorporate within different target media, and tend to migrate from within certain types of media (such as plastics). Furthermore, these two well known types of UV absorbers present handling difficulties in that they are generally produced and utilized in powder form and have relatively low melting points. Particularly, within plastic media, the powder form of these compounds is problematic; a liquid is much easier to handle, does not require melting, and provides more effective and thorough mixing throughout the target plastic. Additionally, these previously utilized UV absorbers provide UV protection over a relatively narrow range of wavelengths ($\lambda_{max}$ from about 290 to about 375 nm for benzotriazoles; from 260 to 340 nm for benzophenones), which ultimately leaves a potentially damaging range of unprotected UV exposure (to about 400 nm). Attempts to increase the amount of such UV absorber compounds in order to provide potential protection over such a broader wavelength range is ineffective, not to mention such greater amounts of UV absorbers increases the production of unwanted colorations within target clear plastics and other like applications such that masking compounds (e.g., bluing agents, for example) must be utilized in relatively high amounts to combat the discoloring effect. Thus, there exists a need to provide a highly effective, liquid ultraviolet absorber which exhibits a versatility to be incorporated within or applied to different and various media and substrates and which, alternatively, can provide protection over the range of wavelengths in the UV spectrum of from about 290 to about 400 nm (in order to provide the best overall protection from possible harm and/or degradation associated with UV exposure).

Methine-based compounds, in particular certain malonate derivatives, as in European Patent Abstract 350-386-A, to L'Oreal SA, are useful as UV absorbers in cosmetic sunscreen compositions, are generally inexpensive to make, and provide UV protection in the spectrum from about 280 to about 360 nm. However, such compounds are highly soluble in organic solvents and could therefore easily migrate from solid compositions, such as plastics, upon introduction therein. Thus, although the utilization of an effective UV absorber, such as a malonate derivative, within plastics, may be highly desirable, such has never been taught nor fairly suggested within the prior UV absorber art due to the great difficulty in producing such a stable, and thus highly effective, UV absorbing composition from such a methine-based source. There exists a need then to produce an inexpensive UV absorber which exhibits the requisite ability to remain within media such as thermoplastics and the like (as noted above), and thus provide necessary and desirable protection from degradation due to UV exposure.

Further developments for the ultraviolet protection of certain polymeric media (such as polyesters) have included methine-based compounds which, to be effective in terms of low extraction from such a thermoplastic, must be introduced during the actual polymerization reaction of the base thermoplastic polymer itself. For example, U.S. Pat. No. 4,617,374 to Pruett et al. teaches such UV absorbers for polyester end-uses. Again, however, such compounds exhibit very high extraction results unless they are added as to-be-polymerized reactants themselves with the ester monomers during the polymerization step. In such an instance, these UV absorbers are actually integrated within the polymer, and not just mixed within the thermoplastic medium. As such, although such compounds do exhibit excellent results when polymerized within the target polyester, unfortunately such compounds are limited in their versatility since the only time during which effective introduction is permitted is during the aforementioned polymerization procedure. There thus still remains a need to provide a more versatile UV absorber for thermoplastic end-uses such that the producer can introduce the UV absorber at any time during the production of the target thermoplastic such that the additive does not exhibit such high extraction and yet still provides excellent UV absorbing properties thereto.

It has now been found that through the addition of polyoxyalkylene chains onto certain ultraviolet absorber compounds, greater versatility of potential uses for the new UV absorber is provided, particularly in terms of the needed low-extraction as noted above. Therefore, it has been found that such polyoxyalkylenated compounds (such as those, without intending to limit the breadth of the invention, the methine-based compounds utilizing vanillin and 4-hydroxybenzaldehyde as starting materials) provide UV absorbers which are highly effective in filtering harmful UV-A and UV-B rays over a broad spectrum ($\lambda_{max}$ from about 280 to about 400 nm, more preferably from about 320 to about 400 nm). Furthermore, it has been found that in combination with a benzotriazole and/or a hydroxybenzophenone, or other similar type of UV absorber compound, the resultant composition is accorded protection from a great amount of potentially damaging UV radiation (from approximately 250 to about 400 nm). Additionally, such a combination is highly stable within the desired media, and thus provides long-term protection to the desired sample stored within the target treated plastic article. Such compounds, when prepared in accordance with certain procedures, most notably with certain alkoxylation catalysts, including, without limitation, metal hydroxides and other bases, both alone and in the presence of amine-based alkoxylation catalysts (particularly with affinities for available protons), as well as rare earth phosphate salts, such as those taught within U.S. Pat. Nos. 5,057,627, 5,057,628, 5,059,719, 5,118,870, 5,208,199, provide the basis for effective utilization within colorless (clear and transparent) applications, such as the desired clear plastics, while simultaneously providing the necessary effective UV protection.

Although some interest has been demonstrated within the area of certain methine-based UV absorber compounds (i.e., L'Oreal's malonate derivatives), to date there has been no disclosure or fair suggestion regarding the utilization of the polyoxyalkylenated derivatives of such UV absorbers in that capacity within certain media (such as, for example, plastics), or on other surfaces (skin, textiles, for example), or in other applications (inks, and the like, for example). In particular, no disclosures exist concerning low-color, low-extraction (migration) polyoxyalkylenated UV absorber compounds that provide effective protection from UV exposure between the wavelengths of from about 320 to about 400 nm. There is thus a great need within the UV absorber market, and most particularly within the transparent plastic film and container markets (for storing and protecting food, pills, and the like) for such types of improvements associated with relatively inexpensive materials and processes provided by the inventive polyoxyalkylenated methine-based UV absorber compounds.

Other ultraviolet absorbing compounds and compositions have been developed or modified for certain plastic (thermoplastic, thermoset, etc.) applications, such as a class of compounds known by the name of Tinuvin®, available from Ciba, and noted above. Although such compounds appear to provide very good ultraviolet protection both to the plastic itself and to any stored liquids, solids, etc., within a container made therewith such plastics, unfortunately such a class of compounds exhibits undesirable or problematic deficiencies. In particular, the breadth of protection within the UV spectrum is generally limited to from about 320 to about 375 nm with such compounds. Thus, they generally do not provide adequate UV protection to contents of plastic packaging over the entire range of UV wavelengths. Also, such Tinuvin-type compounds are generally naturally solid in nature and thus are either dispensed within target resins as solid powders or must be dispersed within liquids by the end-user at time very close to dispensing in order to be effective. If any such Tinuvin-type UV absorbers are in fact liquid, they still are limited in their breadth of UV protection in terms of wavelength ranges. Lastly, such Tinuvin compounds exhibit relatively high extraction levels and migratory characteristics from within target plastic resins, particularly thermoplastics such as polyethylene terephthalates. Thus, although such compounds are effective for UV protection to a certain extent, there are a number of drawbacks for which improvements are highly desired and necessary. To date, there thus remains a great need to provide an effective UV absorber that eliminates the above-noted deficiencies.

OBJECTS OF THE INVENTION

It is therefore an object of this invention to provide novel low-color, low-thermoplastic-migrating (e.g., low-extraction), ultraviolet absorbing compounds, which may further be liquid when present in their pure, undiluted states at room temperature and that provide UV protection over a broad range of wavelengths up to at least 390 nm. A further object of this invention is to provide a polymeric UV absorber that can be used within various media and on different substrates as an effective UV filtering compound or within a suitable composition for protection against potentially harmful ultraviolet rays. A further object of this invention is to provide a methine-based UV absorber that provides clear plastic articles. It is yet another object of this invention to provide certain polyoxyalkylenated methine-based ultraviolet absorbers which do not require the presence of an appreciable amount of bluing agent in order to provide a low-yellowing effect within clear thermoplastic applications (and thus provides brighter clarity within the target plastic or other medium). Yet another object of the invention is to provide an effective UV absorbing composition or article which comprises the inventive low-color, low-thermoplastic-migrating ultraviolet absorbing compounds, particularly with wherein such compounds liquid in nature when undiluted at room temperature. Additionally, an object of this invention is to provide a low-color UV absorber that provides protection to contents within clear thermoplastic packages such that degradation will not readily occur due to exposure to UV wavelengths within the range of 250 to 400 nm.

DESCRIPTION OF THE INVENTION

Accordingly, the present invention thus encompasses an ultraviolet compound conforming to the structure represented by Formula (I)

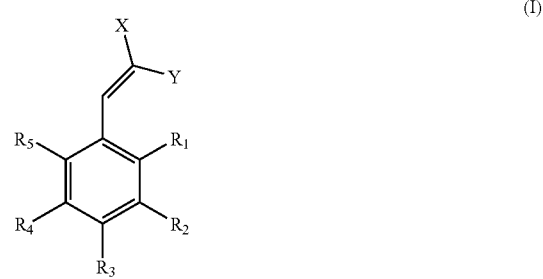

wherein $R_1$, $R_2$, $R_3$, $R_4$, and $R_5$ are the same or different and are selected from the group consisting of $C_{1-20}$ alkyl, halo, hydroxyl, hydrogen, cyano, sulfonyl, sulfo, sulfato, aryl, nitro, carboxyl, $C_{1-20}$ alkoxy, and B-A, wherein at least one of $R_1$, $R_2$, $R_3$, $R_4$, and $R_5$ is B-A, wherein B is selected from the group consisting of N, O, S, $SO_2$, $SO_3$, $CO_2$, and A is represented by the Formula (II)

[polyoxyalkylene constituent]$_z$R'   (II)

wherein polyoxyalkylene constituent is at least three monomers of a monomer selected from the group consisting of $C_{2-20}$ alkyleneoxy group, glydicol, glycidyl, or any mixtures thereof, R' is selected from the group consisting of hydrogen, $C_{1-20}$ alkyl, and $C_{1-20}$ esters; wherein if B is N, then Z is 2, and if B is other than N, then Z is 1; X is hydrogen, cyano, or C(O)OR; Y is hydrogen, cyano, or C(O)OR; wherein if one of X and Y is hydrogen or cyano, then the other is C(O)OR, wherein R is a straight, branched, or cyclic alkyl group having from 4 to 20 carbon atoms. In one preferred embodiment, at least one of $R_2$ and $R_4$ are hydrogen or methoxy, polyoxyalkylene constituent is ethylene oxide, z is 2, B is thus O, X is cyano, and R is either butyl or ethylhexyl. Such a novel compound should exhibit a Gardner color level of at most 10 when present within a methanol solution at a 5% concentration by volume and a maximum ultraviolet absorption within the range of wavelengths of 320 and 400 nm, with a measured ultraviolet transmission of at most 10% at each wavelength under 400 nm, preferably at most 5% under 390 nm, when incorporated at a loading of at most 0.5% by weight within a polyester article having a thickness of at most 1 mm. Also, such a novel compound may also be liquid in its pure, undiluted state at room temperature, again to facilitate handling and introduction within desired media, such as, without limitation, thermoplastics.

Compositions comprising such an inventive UV absorber compound are also encompassed within this invention, particularly those comprising such compounds and bluing agents, as liquids or as pellets for further introduction within desired molten thermoplastic and/or thermoset formulations. Furthermore, end-uses such as the presence of such compounds within solvent systems, printing inks, textile treatment compositions, skin tanning and/or protectant formulations, and the like, may be produced as well for provision of ultraviolet absorbing benefits therein.

The term "thermoplastic" is intended to encompass any synthetic polymeric material that exhibits a modification in physical state from solid to liquid upon exposure to sufficiently high temperatures. Most notable of the preferred thermoplastic types of materials are polyolefins (i.e., polypropylene, polyethylene, and the like), polyester (i.e., polyethylene terephthalate, and the like), polyamides (i.e., nylon-1,1, nylon-1,2, nylon-6 or nylon-6,6), polystyrenes, polycarbonates, polyacrylates, polyvinyl halides (i.e., polyvinyl chloride and polyvinyl difluoride, as merely examples), and the like. Preferred thermoplastics within this invention are polyesters, and most preferred is polyethylene terephthalate. "Thermoset" thus indicates any synthetic polymeric materials that exhibits setting in a pre-oriented position upon exposure to sufficient heat. Most notable are polyurethanes for such applications.

Such thermoplastic and/or thermoset articles include bottles, storage containers, sheets, films, fibers, plaques, hoses, tubes, syringes, and the like. Included within this list would be polyester, polystyrene and other like clear resinous materials in sheet form that are present within windows for strength and resiliency functions. In such an instance, the low-color UV absorbers of this invention would provide or contribute to excellent UV protection for contents with target packaging articles (such as bottles, containers, and the like) or persons located indoors (such as within houses, buildings, cars, and the like, comprising windows with such additives included therein). Basically, the possible uses for such a low-color, low-migratory UV absorber is voluminous and cannot easily be enveloped. Other possible end-uses, however, as noted above, would include solvent systems, printing inks, textile treatment compositions (either on or within textiles, fibers, fabrics), skin tanning and/or protectant formulations, and the like.

Other types of articles contemplated within this invention for the particularly disclosed clear UV protected thermoplastics include, again without limitation, films, sheets, bottles, containers, vials, and the like. Ultraviolet absorbers are typically added to such compositions during the injection molding (or other type of molding, such as blow molding), thereof, including, and without limitation, by mixing the liquid absorber with resin pellets and melting the entire coated pellets, or through a masterbatch melting step while the resin and absorber are pre-mixed and incorporated together in pellet form. Such plastics include, again without limitation, polyolefins, polyesters, polyamides, polyurethanes, polycarbonates, and other well known resins, such as those disclosed within U.S. Pat. No. 4,640,690, to Baumgartner et al., and U.S. Pat. No. 4,507,407, to Kluger et al. under the term "thermoplastics". Generally, such plastics, including the UV absorber additive, are formed through any number of various extrusion, etc., techniques, such as those disclosed in the aforementioned U.S. patents. Preferred thermoplastics are polyesters, such as, in one non-limiting embodiment, polyethylene terephthalate. "Plastic packaging" thus encompasses containers, sheets, blister packages, and the like, utilized for storage purposes and which include the plastics in any combination as noted above.

The term "pure, undiluted state" as used in conjunction with the UV absorbing compounds indicates that the compounds themselves without any additives are liquid at room temperature. Thus, there is no need to add solvents, viscosity modifiers, and other like additives to the UV absorbers to effectuate such a desirable physical state.

Such inventive polymeric UV absorbers, as noted above, are very low in color. Thus, there is no need to add appreciable amounts of other colorants (such as bluing agents, for example), acid scavengers, and other like additives, to the particular UV absorber to provide such desired low-color (low-yellowing) characteristics. It should be well understood by one of ordinary skill in this art that such a benefit as low-yellowing without any other additives present applies solely to the particular compounds and does not indicate that any compositions comprising such compounds solely include such inventive compounds as thermoplastic additives. In fact, other additives, such as the aforementioned bluing agents, acid scavengers, antistatic agents, optical brighteners, and the like, may also be added to these compounds prior to, during, and/or after introduction within the desired end product medium (such as thermoplastic, for example). The polymeric species may be determined through destructive analysis (methanolysis, for example), and further spectrophotometric analysis thereof to locate any signatures of an aniline poly(oxyalkylene) compound, as one example.

The term "solvent systems" encompasses any aqueous or organic liquid formulations. Non-limiting examples of the intended aqueous systems include cleaning solutions, detergents, fabric softeners, marking inks and colorants, and keratin dyes. Non-limiting examples of organic formulations include the non-aqueous types of cleaning solutions, detergents, fabric softeners, marking inks and colorants, keratin dyes, as well as descalers, surfactant formulations, hydrocarbon compositions, and the like. The addition of inventive UV absorbers is accomplished through the mere addition of the liquid compound within the target solvent system with simultaneous and thorough mixing.

Printing inks include compositions utilized as colorants within, again, as merely examples, pens, including, but not limited to ball-point and fountain pens, dot-matrix printers, toners for standard copy machines, ink-jet applications, permanent markers, dry-erase markers, newsprint, magazine print, laser jet printers, and the like. The addition of inventive UV absorbers is accomplished through the mere addition of the liquid compound within the target printing ink formulations with simultaneous and thorough mixing.

The term "textile treatment compositions" comprises both any formulations for application on textiles (and thus leaving at least a temporary UV absorbing coating, or the like, on the textile surface). Incorporation of the inventive compounds within fibers of textiles is also encompassed within this term and thus within this invention. Skin protectant and skin tanning formulations basically encompass any compositions comprising the novel UV absorbing compound that is utilized to protect skin from solar radiation.

The benefits accorded by the aforementioned novel ultraviolet absorbing compounds are plentiful, considering the state of the art at this time. For example, clear thermoplastic or thermoset article are highly desirable in order to facilitate recognition of compositions and formulations contained within such articles, for evident reasons. For aesthetic purposes, such clear articles should not exhibit any discoloration. With most standard UV absorbers used today, yellowing is prevalent due to the inherent nature of the compounds themselves providing such color in order to absorb within the UV range. Thus, as noted previously, bluing agents, in relatively high amounts, are required to counter this effect and provide the desired uncolored resin. The inventive plastic compositions and/or formulations (and inventive ultraviolet absorber compounds) do not exhibit such discolorations to such a degree and thus, even though some yellowing may be exhibited by such compounds, and thus within the target thermoplastics, the use of much lower amounts of bluing agents provides the needed clear, uncolored resin, thereby saving on cost and reducing the work needed to provide such a proper clear article as well as a brighter article. Because bluing agents not only aid in preventing yellowness within target media, but also contribute grayness therein as well, the utilization of large amounts of such agents is generally avoided. The inventive compounds thus provide clarity with low grayness levels due to the low-color aspects available therewith. As a result, the desired clear plastics exhibit heretofore unattained brightness levels with simultaneously extensive and effective ultraviolet protection over a wide range of wavelengths (as discussed above). Furthermore, such effective UV absorbing characteristics are noticeable in terms of protection for certain contents of target thermoplastic storage articles.

Furthermore, such inventive compounds exhibit extremely low migratory (e.g., low-extraction) levels from plastics and other media. The presence of poly(oxyalkylene) chains thereon provides a very versatile UV absorbing compound as a liquid or low viscosity additive that, exhibits thorough and effective mixing when introduced within the target thermoplastic and following molding and cooling also exhibits very low extraction levels therefrom. Such resultant low extraction levels are exhibited by said inventive compound (as well as said inventive thermoplastic compositions and/or formulations) no matter when the inventive UV absorber compound is introduced within the target thermoplastic during production thereof. Thus, introduction at the polymerization stage (as in Pruett et al.), as well as at the injection molding stage, or even during the initial mixing stage of the target thermoplastic with its additives, all accord a very low-extraction result for the inventive UV absorbers. Such versatility thus permits the user to set up his reaction method in terms of other limitations, rather than on the limits imposed by the effective introduction of a low-extraction UV absorber compound (as now is the case in Pruett et al.). Such a benefit thus accords the user the flexibility to introduce the necessary effective UV absorber at any time during thermoplastic production. Hence, introduction of such polymeric compounds within the target resins at any time during the production method is facilitated by the liquid nature of most of the inventive polymeric UV absorber compounds including reactive terminal functional groups. Handling is greatly improved thereby, and more thorough dispersion within the desired medium is accomplished as well. Again, costs are reduced due to simplicity and reliability is increased with more thorough mixing, etc., through utilization of such inventive compounds with simultaneous or concomitant reliability in terms of performance and low extraction characteristics.

Additionally, such a highly reliable, easy-to-handle, low-color, and low-migratory (low-extraction) UV absorbing compound also provides a greater range of protection than the standard UV absorbers now provided within the industry. Generally, such standard UV absorbers are effective up to about 375 nm, even with an increase in amount of such a compound within the target medium (polyester, for example). Even with increased amounts of such standard UV absorbers present within the target media (such as thermoplastics), the discolorations within the target medium are more pronounced without a correlated benefit in a greater range of protected wavelengths. To the contrary, the inventive compounds provide protection up to about 400 nm. This effect is easily shown through the selection of a certain chemical compound prevalent within stored liquids and solids that is highly susceptible to UV attack and decomposition. For instance, in comparison with standard UV absorbers (Tinuvin® 234, for example), the protection accorded riboflavin within an aqueous solution and stored within a clear polyethylene terephthalate container and exposed to a UV source between 320 and 400 nm for 20 hours is significantly higher for similar non-polymeric, non-methine type ultraviolet absorbers. Such an improvement, in combination with any or all of the other characteristics exhibited by these inventive compounds, thus shows the novelty and usefulness of such compounds, particularly within clear, and possibly plastic, applications.

In particular, such inventive UV absorbing compounds then conform to the following structure (I)

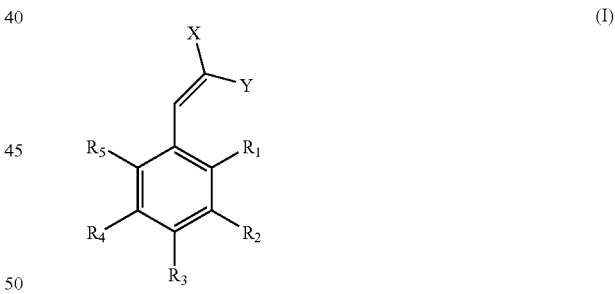

(I)

wherein $R_1$, $R_2$, $R_3$, $R_4$, and $R_5$ are the same or different and are selected from the group consisting of $C_{1-20}$ alkyl, halo, hydroxyl, hydrogen, cyano, sulfonyl, sulfo, sulfato, aryl, nitro, carboxyl, $C_{1-20}$ alkoxy, and B-A, wherein at least one of $R_1$, $R_2$, $R_3$, $R_4$, and $R_5$ is B-A, wherein B is selected from the group consisting of N, O, S, $SO_2$, $SO_3$, $CO_2$, and A is represented by the Formula (II)

[polyoxyalkylene constituent]$_z$R'  (II)

wherein polyoxyalkylene constituent is at least three monomers of a monomer selected from the group consisting of $C_{2-20}$ alkyleneoxy group, glydicol, glycidyl, or any mixtures thereof, R' is selected from the group consisting of hydrogen, $C_{1-20}$ alkyl, and $C_{1-20}$ esters; wherein if B is N, then Z is 2, and if B is other than N, then Z is 1; X is hydrogen, cyano, or C(O)OR; Y is hydrogen, cyano, or C(O)OR, wherein if one of X and Y is hydrogen or cyano, then the other is C(O)OR, wherein R is a straight, branched, or cyclic alkyl group having from 4 to 20 carbon atoms. In one preferred embodiments, at least one of $R_2$ and $R_4$ are hydrogen or methoxy, polyoxyalkylene constituent is ethylene oxide or propylene oxide (between 3 and 100 units of such monomers; preferably between 3 and 50; and most preferably, between 4 and 20), z is 2, B is thus N, X is cyano, and R is either butyl or ethylhexyl, or longer chained (such as octyl, etc.). Also, in one potentially preferred embodiment $R_2$ is hydrogen, methoxy, or ethoxy. Such compounds thus must also exhibit the aforementioned low-color and low-migration (from the target medium, such as plastic) characteristics, as well as existing as a liquid when in its undiluted state at room temperature.

Such compounds are poly(oxyalkylenated) in order to provide the desired low extraction levels from thermoplastics as discussed above. The ability to provide such low-color species for the structure conforming to Formula (I) is apparently controlled through the utilization of specific types of alkoxylation catalysts, including, without limitation, rare earth salts (such as lanthanum phosphates), particular metal hydroxides (such as potassium hydroxide both alone and in the presence of compounds having a strong affinity for free and/or available protons within the reaction medium itself, hereinafter referred to as "proton sponge"), and the like. Such catalysts, particularly the rare earth phosphates, apparently are configured in such a way that the levels of impurities and starting materials present within the reaction itself if drastically reduced in comparison with other standard alkoxylation catalysts (such as sodium hydroxide) (although the true reasons behind such beneficial low-color production is not completely understood). Preferred are lanthanum phosphate catalysts which are white powdery materials having a mean particle size (D50) of between 5 and 50 microns, a lanthanum, content of at least 58% by weight, and is substantially free from any chlorine. The poly(oxyalkylenated) products catalyzed therefrom generally exhibit much less color in comparison with other standard alkoxylation catalysts (such as NaOH, as noted previously). Such a preferred catalyst is the same utilized within the particular examples below.

Furthermore, without intending to be limited to any specific scientific theory, it is postulated that such aforementioned proton sponge compounds prevent the potentially deleterious reaction of strongly charged proton species from attacking the final reactants and reaction products and thus curtails the production of discoloring compounds within the final product itself. Examples of such proton sponge compounds include, without limitation, 1,8-bis(dimethylamino) naphthalene, 1,8-bis(diethylamino)-2,7-dimethoxynaphthalene, 4,5-bis(dimethylamino)-fluorene, 4,5-bis (dimethylamino)phenanthrene, quino[7,8-n]quinoline, and the like, with 1,8-bis(dimethylamino)naphthalene preferred.

Preferably, the alkoxylated compounds include either ethylene oxide or propylene oxide, or mixtures of both, thereon having chain lengths from 3 to about 100; more preferably such a chain length if from about 3 to about 50; and most preferably such a chain length is from about 4 to about 20, with all ethylene oxide also highly preferred.

Compositions comprising such compounds are also encompassed within this invention, particularly those of the compounds and bluing agents as liquids or as pellets. These broadly defined compounds as well as the more specific types thus provide the necessary characteristics for clear applications (again, clear plastics, as one non-limiting example) in terms of low color, low migration, liquid state, and effective and thorough mixing within the target medium.

The proper amounts utilized in the various compositions and applications are highly dependent on each of those separate possibilities. Thus, in plastics, for example, the inventive UV absorber is added in an amount of from about 0.001 to about 1.5% by weight of the total plastic composition, preferably from about 0.01 to about 1.0%, and most preferably from about 0.05 to about 0.5%. Such plastics may include other standard additives, including antioxidants, clarifying agents, nucleators, acid scavengers, perfumes, colorants (for transparent, but colored applications), antistatic agents, and the like.

DESCRIPTION OF THE PREFERRED EMBODIMENTS

The general methods of making and utilizing the preferred inventive UV absorbers are as following:

Preparation of Compounds, Synthesis of UV Absorbers

EXAMPLE 1 (FOR INVENTIVE AND COMPARATIVE EXAMPLES)

4-Hydroxybenzaldehyde 5EO

Four hundred grams of 4-hydroxybenzaldehyde, 400 ml of toluene and 4 grams of lanthanum phosphate catalyst were charged to an autoclave. The autoclave was then sealed, purged several times with nitrogen gas (to a pressure of 60 PSIG) and then pressurized to 5 PSIG of nitrogen. After heating the autoclave to 121° C., ethylene oxide was added to the reaction mixture until a total of 722 grams were added over time. Once all of the ethylene oxide was added, the mixture was post-cooked for a total of thirty minutes. The mixture was then cooled to 93° C. and vacuum stripped for fifteen minutes in order to remove un-reacted ethylene oxide. After stripping off toluene, a total of 1110 grams (99%) product is obtained as a pale yellow liquid with a hydroxyl number of 163.

EXAMPLE 2 (COMPARATIVE)

4-Hydroxybenzaldehyde 5EO/ECA UV Absorber

To a 250-ml 3-neck flask, were charged with 100 grams of 4-hydroxybenzaldehyde 5EO from Example 1, 34.6 grams of ethyl cyanoacetate (ECA) and 8 grams of ammonium acetate. The reaction was allowed to heat to 50° C. for 3 hours in the presence of a nitrogen atmosphere. Upon cooling to room temperature, 200 ml of water were added and the mixture heated to 75° C. After phasing, the product layer was washed again with 200 ml of water. Removal of water via rotary evaporator yielded 100 g of product that has a lambda max of 340 nm in methanol and color value of 62 (abs/g/L).

EXAMPLE 3

4-Hydroxybenzaldehyde 5EO/BCA UV Absorber

To a 250-ml 3-neck flask, were charged with 100 grams of 4-hydroxybenzaldehyde 5EO from Example 1, 44 grams of butyl cyanoacetate (BCA) and 8 grams of ammonium acetate. The reaction was allowed to heat to 50° C. for 3 hours in the presence of a nitrogen atmosphere. Upon cooling to room temperature, 200 ml of water were added and the mixture heated to 75° C. After phasing, the product layer was washed again with 200 ml of water. Removal of water via rotary evaporator yielded 117 g of product that has a lambda max of 341 nm in methanol and color value of 65 (abs/g/L).

EXAMPLE 4

4-Hydroxybenzaldehyde 5EO/EHCA UV Absorber

To a 250-ml 3-neck flask, were charged with 50 grams of 4-hydroxybenzaldehyde 5EO from Example 1, 30.5 grams of 2-ethylhexyl cyanoacetate (EHCA) and 4 grams of ammonium acetate. The reaction was allowed to heat to 50° C. for 3 hours in the presence of a nitrogen atmosphere. Upon cooling to room temperature, 100 ml of water were added and the mixture heated to 75° C. After phasing, the product layer was washed again with 100 ml of water. Removal of water via rotary evaporator yielded 59 g of product that has a lambda max of 341 nm in methanol and color value of 52 (abs/g/L).

EXAMPLE 5 (FOR INVENTIVE AND COMPARATIVE EXAMPLES)

Vanillin 6EO

Two thousand two hundred and eighty grams of vanillin, 20 g of lanthanum phosphate catalyst were charged to an autoclave. The autoclave was then sealed, purged several times with nitrogen gas (to a pressure of 60 PSIG) and then pressurized to 5 PSIG of nitrogen. After heating the autoclave to 121° C., ethylene oxide was added to the reaction mixture until a total of 3960 g were added over time. Once all of the ethylene oxide was added, the mixture was post-cooked for a total of thirty minutes. The mixture was then cooled to 93° C. and stripped at reduced pressure for fifteen minutes in order to remove un-reacted ethylene oxide. The product is a pale yellow liquid with a hydroxyl number of 134.

EXAMPLE 6 (COMPARATIVE)

Vanillin 6EO/ECA UV Absorber

One hundred grams of 4-polyoxyalkylene-3-methoxybenzaldehyde from the reaction described in Example 5, 8.5 g of ammonium acetate, and 28 g of ethyl cyanoacetate (ECA) were charged to a 500 ml three neck round bottom flask. The reaction mixture was purged for five minutes with nitrogen and next heated to 40° C. and held for three hours. Upon cooling to room temperature, 200 ml of water was added and the mixture heated to 75° C. After phasing, the product layer was washed again with 200 ml of water. Removal of water via a rotovap yielded 94 g of product that has a lambda max of 358 nm in methanol. Its color value in methanol, which is defined as absorption per gram of sample in 1000 ml of methanol, is 43 abs/g/l.

EXAMPLE 7

Vanillin 6EO/BCA UV Absorber

One hundred grams of 4-polyoxyalkylene-3-methoxybenzaldehyde from the reaction described in Example 5, 8.5 g of ammonium acetate, and 35 g of butyl cyanoacetate (BCA) were charged to a 500 ml three neck round bottom flask. The reaction mixture was purged for five minutes with nitrogen and next heated to 40° C. and held for three hours. Upon cooling to room temperature, 200 ml of water was added and the mixture heated to 75° C. After phasing, the product layer was washed again with 200 ml of water. Removal of water via a rotovap yielded 103 g of product that has a lambda max of 358 nm in methanol. Its color value in methanol, which is defined as absorption per gram of sample in 1000 ml of methanol, is 42 abs/g/l.

EXAMPLE 8

Vanillin 6EO/EHCA UV Absorber

One hundred grams of 4-polyoxyalkylene-3-methoxybenzaldehyde from the reaction described in Example 5, 8.5 g of ammonium acetate, and 51 g of 2-ethylhexyl cyanoacetate (EHCA) were charged to a 500 ml three neck round bottom flask. The reaction mixture was purged for five minutes with nitrogen and next heated to 40° C. and held for three hours. Upon cooling to room temperature, 200 ml of water was added and the mixture heated to 75° C. After phasing, the product layer was washed again with 200 ml of water. Removal of water via a rotovap yielded 86 g of product that has a lambda max of 358 nm in methanol. Its color value in methanol, which is defined as absorption per gram of sample in 1000 ml of methanol, is 37 abs/g/l.

Performance of UV Absorbers in Polymers

Thermoplastic Composition Formation in PET

In each instance noted below regarding polyester article production applications, the inventive polymeric UV absorber was introduced within an injection molding operation for a polyester thermoplastic, in this instance polyethylene terephthalate (ClearTuf® 8006 PET resin from M&G). The inventive UV absorber, in the amount noted in the related examples below, was blended via agitation onto hot, dried PET resin pellets. The blend of UV absorber and pellets was gravity fed into the feed throat of the machine. In the feed section, melting was accomplished through the utilization of rotating heated (heat transferred from the barrel of the machine) screw extruder. The rotation of the screw provided thorough mixing of the UV absorber and molten resin together producing a uniform plastic melt which was injected into a mold in order to form the thermoplastic article, in this instance a 2 inch by 3 inch plaque with a uniform thickness of 50 mils and a surface area of 12.5 in$^2$.

Thermal Stability of Inventive UV Absorber in PET

Ten plaques of UV absorber-containing PET, as made above, thermoplastic plaques of polyester terephthalate containing inventive UV absorber were produced as described above (injection molded) were collected. The same injection molding machine used to produce these first ten plaques [Control Samples] was then was paused during production of ten further plaques and allowed to remain idle for 15 minutes at the standard polyester processing temperatures (~277° C.). At the end of the 15-minute pause, the machine was then restarted without purging the colored resin from the heated barrel of the machine. Ten consecutive plaques [Measured Samples] were then collected and numbered after resumption of the injection molding operation.

The absorbance at the UV absorber lambda max of the Control Samples collected from the standard operation was measured by Perkin-Elmer Lambda 35 Spectrophotometer and averaged together to represent a standard measurement for all plaques. Each of the ten consecutive Measured Sample plaques collected after the 15-minute hold-period was measured individually and sequentially on the spectrophotometer. The absorbance difference between the standard measurement for the Control Samples each of the ten Measured Sample plaques was recorded and defined as the change in absorbance ($\Delta Abs$). The thermal stability of UV absorber was measured by the percentage of UV absorbance loss (Loss %), as calculated by the formula Loss %=[$\Delta Abs$]/[standard]

The biggest Loss % of the ten Measured Samples plaques collected after the 15-minute hold period represents the largest absorbance difference, and is determined to be the UV absorber's thermal stability.

The thermal stability (Loss %) of the inventive UV absorbers from Example 2, 3, 6, and 7, above, were measured, and the results are tabulated below (the loading for UV absorber Example 2 was 822 ppm, and the other samples' loadings were adjusted to the same heights of the absorption peaks based on their Color Values):

TABLE 1

Inventive UV Absorber Thermal Stability Data in PET

| UV Absorber Composition | Loss % |
|---|---|
| From Example 2 | 2.3 |
| From Example 3 | 1.1 |
| From Example 6 | 8.9 |
| From Example 7 | 0.5 |

A Loss % of less than 10 is considered to be acceptable, with a result below 2% considered to be excellent when analyzed by this protocol. Clearly, the inventive UV absorbers exhibit highly favorable thermal stability characteristics, particularly in comparison with the comparatives of Examples 2 and 6.

Lightfastness of Inventive UV Absorber in PET

For each individual inventive UV absorber compositions at specified loadings (below), ten plaques were made according to process described as above in the previous section.

The absorbance (at each inventive UV absorber's lambda max) of the ten plaques collected from the standard operation was measured in Perkin-Elmer Lambda 35 Spectrophotometer and averaged together to represent the Standard Measurement. Three sets of 2 plaques were then placed under xenon light for 10, 20 and 40 hours exposure, respectively. Each set of the 2 plaques was collected after the elapsed times of exposure and were measured for change in absorbance (at each inventive UV absorber's lambda max) individually and sequentially on a Perkin-Elmer spectrophotometer. The absorbance difference between the Standard Measurement and each of the 3 sets of plaques exposed was determined as $\Delta Abs$. The lightfastness of the incorporated UV absorber was thus measured by the percentage of UV absorbance loss (Loss %), as calculated by the formula Loss %=[$\Delta Abs$]/[Standard]

The greater the Loss % of the plaques, the larger the absorbance difference and is determined to be worse the UV absorber's lightfastness.

TABLE 2

Lightfastness of the Inventive UV Absorber

| UV Absorber Composition | Loading | Exposure Time | Loss % |
|---|---|---|---|
| From Example 2 | 123 ppm | 10 hours | 18.1 |
|  |  | 20 hours | 19.2 |
|  |  | 40 hours | 20.5 |
| From Example 3 | 118 ppm | 10 hours | 13.3 |
|  |  | 20 hours | 13.8 |
|  |  | 40 hours | 15.0 |
| From Example 6 | 212 ppm | 10 hours | 12.1 |
|  |  | 20 hours | 16.5 |
|  |  | 40 hours | 16.8 |
| From Example 7 | 217 ppm | 10 hours | 8.1 |
|  |  | 20 hours | 8.5 |
|  |  | 40 hours | 9.8 |

Under this protocol, a Loss % of at most 15% after 40 hours exposure and at most 14% after 20 hours exposure are highly desired. This shows that the Inventive Examples of 3 and 7 provide improved lightfastness over the Comparatives. Thus, the inventive UV absorbers exhibit highly desired, unexpectedly good lightfastness characteristics.

Determination of Yellowness of UV Absorbers in Molded PET

The degree of yellowing as a result of processing was determined for selected UV absorber examples. A specified amount of inventive UV absorber was added to 2 kg of ClearTuf® 8006 polyester resin. After thorough mixing, the resin was compounded on a Single-Screw extruder and the emergent strands of material were pelletized. To simulate the industrial drying process commonly practiced by the converters, one half of the pelletized sample was dried at 150° C. under vacuum for five hours and afterwards injection molded into 175 mil thickness plaques (2 in×3 in). To simulate the industrial Solid Stating Process (SSP) commonly practiced by PET resin manufacturers, the other half of the pelletized sample was subjected to a drying process at 210° C. under a nitrogen atmosphere for 15 hours and afterwards injection-molding the pellets into 175 mil thickness plaques (2 in×3 in). The degree of yellowing of the plaques, expressed as Yellowness Index (ASTM Test Method E-313) was quantified with the aid of a MacBeth Coloreye 7000 spectrophotometer.

The yellowness of the inventive UV absorbers from Example 2, 3, 6, and 7 in PET after solid stating were measured, and the results are tabulated below:

TABLE 3

Yellowness of the Inventive UV Absorber in Molded PET

| UV ABSORBER | LOADING | YELLOWNESS INDEX | |
|---|---|---|---|
|  |  | 150° C., 5 hrs | SOLID STATING |
| PET Control | — | 1.5 | 3.5 |
| EXAMPLE 2 | 823 ppm | 5.6 | 11.4 |
| EXAMPLE 3 | 785 ppm | 3.5 | 7.5 |
| EXAMPLE 6 | 1698 ppm | 20.2 | 27.0 |
| EXAMPLE 7 | 1738 ppm | 20.6 | 27.0 |

Under this testing protocol, a Yellowness Index of at most 30 at the suggested loading levels is considered to be acceptable by the industry. Most of the Inventive examples exhibited far better yellowness ratings than the Comparatives, showing the unexpectedly good results provided thereby.

While specific features of the invention have been described, it will be understood, of course, that the invention is not limited to any particular configuration or practice since modification may well be made and other embodiments of the principals of the invention will no doubt occur to those skilled in the art to which the invention pertains. Therefore, it is contemplated by the appended claims to cover any such modifications that incorporate the features of the invention within the true meaning, spirit, and scope of such claims.

What is claimed is:

1. An ultraviolet light absorbing compound conforming to the structure represented by Formula (I)

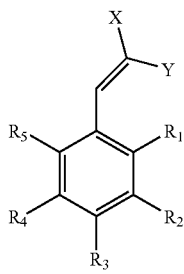

(I)

(a) wherein $R_1$, $R_2$, $R_3$, $R_4$, and $R_5$ are selected from the group consisting of: $C_{1-20}$ alkyl, halo, hydroxyl, hydrogen, cyano, sulfonyl, sulfo, sulfato, aryl, nitro, carboxyl, $C_{1-20}$ alkoxy, and B-A, (b) further wherein at least one of $R_1$, $R_2$, $R_3$, $R_4$, and $R_5$ is B-A,
　i) wherein B of said B-A is selected from the group consisting of O, S, $SO_2$, $CO_2$, and
　ii) wherein A of said B-A is represented by the Formula (II);

[polyoxyalkylene constituent]-R'　　　II said polyoxyalkylene constituent comprising at least three monomer units, said monomer units selected from the group consisting of:

$C_{2-20}$ alkyleneoxy group, glydicol, glycidyl, or any mixtures thereof;

R' is selected from the group consisting of: hydrogen, $C_{1-20}$ alkyl, $C_{1-20}$ alkoxy, and $C_{1-20}$ esters;

(c) X is selected from the group consisting of: cyano and COOR; Y is selected from the group consisting of: cyano and COOR; wherein one of said X or Y is cyano and the other is COOR; further wherein said R of said COOR is a butyl group, said butyl group having four carbons in a straight or branched configuration.

* * * * *